United States Patent [19]

Rose et al.

[11] Patent Number: 4,677,061
[45] Date of Patent: Jun. 30, 1987

[54] T-CELL LYMPHOCYTE SUBSET MONITORING OF IMMUNOLOGIC DISEASE

[75] Inventors: Lynn M. Rose; Edward A. Clark; Jeffrey A. Ledbetter, all of Seattle, Wash.

[73] Assignee: Genetic Systems Corporation, Seattle, Wash.

[21] Appl. No.: 662,878

[22] Filed: Oct. 19, 1984

[51] Int. Cl.$^4$ ..................... C12Q 1/06; G01N 33/566
[52] U.S. Cl. .......................................... 435/39; 435/29; 435/34; 435/7; 436/501; 436/543; 436/546; 424/7.1; 424/85
[58] Field of Search ............... 436/501, 546, 547, 548, 436/543; 435/29, 34, 39, 7; 422/61; 424/7.1, 85

[56] References Cited

U.S. PATENT DOCUMENTS 4,311,686  1/1982  Angers et al. ................ 436/508

OTHER PUBLICATIONS

Gatenby, Paul A., Kansas, Geoffrey S., Xian, Chen Yu, Evans, Robert L. and Engleman, Edgar G., "Dissection of Immunoregulatory Subpopulations of T Lymphocytes within the Helper and Suppressor Sublineages in Man," J. Immunol., 129:1997-2000 (1982).

Lanier, L. L., Engleman, E. G., Gatenby, P., Babcock, G. F., Warner, N. L. and Herzenberg, L. A., "Correlation of Functional Properties of Human Lymphoid Cell Subsets and Surface Marker Phenotypes Using Multi--parameter Analysis and Flow Cytometry," Immunol. Rev., 74:143-160 (1983).

Lanier, Lewis L., Le, An My, Phillips, Joseph H., Warner, Noel L., and Babcock, George F., "Subpopulations of Human Natural Killer Cells Defined by Expression of the Leu-7 (HNK-1) and Leu-11 (NK-15) Antigens," J. Immunol., 131:1789-1796 (1983).

Lanier, Lewis L. and Loken, Michael R., "Human Lymphocyte Subpopulations Identified by Using Three-color Immunofluorescence and Flow Cytometry Analysis: Correlation of Leu-2, Leu3, Leu-7, Leu-8 and Leu-11 Cell Surface Antigen Expression," J. Immunol., 132:151-156 (1984).

Medical Intelligence, Reinherz, Ellis, L. and Schlossman, Stuart F., Current Concepts in Immunology, Regulation of the Immune Response—Inducer and Suppressor T-Lymphocyte Subsets in Human Beings," New England J. Med., 303:370-373 (1980).

Hauser, Stephen L., Reinherz, Ellis L., Hoban, Carolyn J., Schlossman, Stuart F. and Weiner, Howard L., "Immunoregulatory T-Cells and Lymphocytotoxic Antibodies in Active Multiple Sclerosis: Weekly Analysis over a Six-month Period," Annals of Neurol., 13:418-425 (1983).

Dalchau, R. and Fabre, J. W., "Studies on the Distribution Among T Lymphocytes of the High-Molecular--Weight Form of the Human Leucocyte Common Antigen," Leukocyte Typing, eds. Bernard, A., Boumsell, L. et al., p. 507, Springer-Verlag, Berlin.

Hayakawa, Kyoto, Hardy, Richard R., Parks, David R. and Herzenberg, Leonore A., "The 'LY-1 B' Cell Subpopulation in Normal, Immunodefective, and Autoimmune Mice," J. Exp. Med., 157:202-218 (1983).

Primary Examiner—Christine M. Nucker
Assistant Examiner—Stephen C. Wieder
Attorney, Agent, or Firm—Townsend and Townsend

[57] ABSTRACT

Methods and compositions are provided for determining a change in status of a multiple sclerosis victim. Particularly, the ratio of helper or suppressor T cell subsets having specific surface markers associated with proliferation is determined, where a particular ratio value is associated with a change in status.

14 Claims, No Drawings

T-CELL LYMPHOCYTE SUBSET MONITORING OF IMMUNOLOGIC DISEASE

BACKGROUND OF THE INVENTION

1. Field Of The Invention

Multiple sclerosis (MS) is a chronic, often disabling disease of the central nervous system. Clinically, MS is highly variable and there is no specific diagnostic test. In a large proportion of the patients, the disease is manifested by unpredictable attacks called exacerbations followed by quiescent periods called remissions. The duration of these remissions is uncertain and exacerbations are not predictable.

At present, the cause of MS is not known and there is no known cure. However, there is evidence which is consistent with an agent, such as a virus, which leads to a defective "autoimmune" response. Treatment of the disease involves the use of steroids and other drugs which can have serious side effects and whose administration for prolonged periods is undesirable. To the extent that these drugs could anticipate an exacerbation, to inhibit or diminish the disorienting effects of the exacerbation, it would be desirable to be able to predict the onset of an exacerbation. In addition, the ability to predict a remission would also be useful, so that treatment during the exacerbation could be rapidly terminated at the earliest time. Furthermore, a means of diagnosing or confirming the diagnosis of MS would be extremely useful.

2. Brief Description Of The Prior Art

Lisak et al., Clin. Exp. Immunol (1975) 22:30–34 suggested that autoimmunity plays a role in multiple sclerosis. The presence of abnormalities in T-cell subsets as determined with a monoclonal antibody to the TP 32 cell surface antigen was reported by Werner and Hauser, Ann. Neurol. (1982) 11:437 and Oger et al., Neuro. Clinica. (1983) 1:655, as well as Reinherz and Schlossman, N. Eng. J. Med. (1980) 303:125, who reported that there were T suppressor cell deficiencies. See also Hauser et al., Ann. Neurol. (1983) 13:418–425. Results, contrary to the results reported in the above citations, have been published in studies by Kastrukoff and Paty, Ann. Neurol. (1984) 15:250–256 and Paty et al., Ibid. (1983) 14:455.

The use of multiple parameter flow cytometric analysis for the study of normal human peripheral blood lymphocytes is exemplified in Hardy et al., Ann. N.Y. Acad. Sci. (1982) 399:112, Lanier and Loken, J. of Immunol. (1984) 132:151, Lanier et al., Ibid. (1983) 131:1789 and Lanier et al., Immunological Rev. (1983) 74:143.

SUMMARY OF THE INVENTION

Methods and compositions are provided for the diagnosis and determination of changes in disease activity in victims of immunological disease, especially multiple sclerosis. Particularly, ratios of subsets of CD4+ (helper) cells and or CD8+ (suppressor) cells differentially expressing membrane surface antigens associated with cellular differentiation are determined and related to predetermined ratios as indicative of the presence of disease or of a change in disease activity. The information can be used in conjunction with monitoring and treatment of MS and other immunologic disease victims.

DESCRIPTION OF THE SPECIFIC EMBODIMENTS

Methods, compositions and kits are provided for the diagnosis and/or detection of change of disease activity in a human host having or suspected of having an immunologic disease, especially multiple sclerosis (MS). Particularly, T cell subsets are monitored for a designated pattern of epitopic sites associated with specific surface membrane proteins, where ratios of cells having different patterns are conveniently determined by multi-parameter flow cytometric analysis, the ratios being indicative of a probable change in MS disease activity. By change of MS disease activity is intended changes referred to as exacerbation and remission, although the same parameters may also be used to monitor the status of patients in chronic progressive phase. The same parameters may also aid in the differential diagnosis of MS and in the diagnosis and monitoring of other forms of immunologic disease, such as juvenile rheumatoid arthritis, systemic lupus erythematosus, acquired immunodeficiency syndrome, etc., in which changes in the conventionally measured $T_h/T_s$ (CD4+/CD8+) ratio are known or suspected to occur.

Of particular interest are subsets of CD4+ (helper or $T_h$) cells and CD8+ (suppressor or $T_s$) cells (Bernard et al., Eds. 1984, *Leukocyte Typing*, Springer Verlag, Berlin, Page 133). CD4+ cells express the TpS5 cell surface antigen, while CD8+ cells express the Tp32 cell surface antigen. Subsets of these cells are defined by the relative co-expression of surface membrane proteins found to be associated with cell differentiation. (By differentiation is intended an antigen which distinguishes one or more cell types or groups from other cell types or groups and which may be present or absent at varying stages during the maturation of a cell.) Particularly, the ratio of cells in a particular subset bearing a high level of one or more surface membrane proteins associated with differentiation in contrast to cells of the same subset, lacking or having a readily distinguishable lower amount of one or more of the surface membrane proteins, is determined.

Usually, it will be sufficient to have a single epitopic site for the designation of each cell subset and one may have from one to four, conveniently one to two additional epitopic sites whose differential co-expression is monitored. Of particular interest for CD4+ cells is the presence or absence of Lp220, which is recognized by the antibody 3AC5; and Lp95-150 (CDW18), recognized by antibody 60.3, (Beatty et al., J. Immunol. (1983) 131:2913) with CD8+ cells. Either or both ratios of CD4+ Lp220−/CD4+ Lp220+ and CD8$^{bri}$ Lp95-150$^{bri}$/CD8$^{bri}$ Lp95-150$^{dull}$ (bri intends bright) may be employed individually or together for the diagnosis or detection of a change in disease activity of a human having or suspected of having MS or other immunologic disease.

Various techniques may be employed for the determination of the ratios of cells having the specified pattern of antigen expression. A wide variety of techniques exists for measuring the presence of specific antigens on cells using a wide variety of labels, such as radionuclides, fluorescers, chemiluminescers, particles, enzymes, enzyme substrates or cofactors or inhibitors, or the like. However, at the present time, for determination of the presence of a multiplicity of epitopic sites on a specific cell, the preferred technique is multi-parameter flow cytometric analysis (Herzenberg and Herzenberg, 1978, *Analysis and Separation Using The Fluores-*

*cence Site-Activated Cell Sorter (FACS)*. In: A Handbook of Experimental Immunology, 3rd Ed. Weir, D. B., p. 221, Blackwell Scientific Publications, London). This method involves conjugating antibodies specific for different epitopic sites either directly or indirectly, with fluorescers, different fluorescers being used for each site, and employing a cell sorter with multicolor analysis. By employing fluorescers having different emission peaks, one provides for independent detection of each of the epitopic sites.

Of particular interest is the employment of fluorescers providing for long Stokes shifts ($\geq 25$ nm), absorbing below about 520 nm, preferably below about 500 nm and emitting above about 525 nm. The antibodies to the specific surface membrane proteins may be directly conjugated to the fluorescers, or they may be indirectly labelled, that is, the fluorescer may be covalently linked to the antibody or non-covalently linked through ligand-receptor complex formation, e.g. hapten-antibody, anti-Ig antibody, or biotin-avidin. For example, by employing antibodies for each of the epitopic sites from different hosts, fluorescing antibodies may be employed which are directed to the immunoglobulin of the particular host. Alternatively, the primary antibody can be biotinylated and reacted with fluorescerconjugated avidin.

Various fluorescers find use, such as fluorescein, rhodamine, Texas red, phycobiliproteins, such as phycoerythrin, allophycocyanin, phycocyanin, phycoerythrocyanin, and the like, umbelliferone, dansyl, etc.

In carrying out the assay, blood samples are taken from a patient, particularly peripheral blood, and the desired cells isolated by conventional techniques and suspended in an appropriate medium. Particularly, the blood sample may be introduced into a heparinized receptacle, diluted 1:1–1:5 in a conventional tissue culture medium, layered on a lymphocyte separation medium such as Ficoll-Hypaque, and the interface mononuclear cells washed and resuspended at a concentration of about $10^5$–$10^8$/ml in a tissue culture medium with appropriate adjuvants. Alternatively, a whole blood sample in which the red blood cells have been lysed by addition of an appropriate agent, such as ammonium chloride, can be utilized. The cell suspension may then be incubated at moderate temperatures ($-5°$–$25°$ C.) with the appropriate antibodies (in two stages where the labeling is indirect), these cells washed and then freed of agglomerated cells, conveniently by passing through a micropore filter. The amount of antibody employed will be about 1–3 doubling dilutions above the titration end point. The suspension is now ready for use in a cell sorter or analyzer in accordance with conventional techniques, further details being provided in the Experimental Section.

For diagnosing the probability of a change in disease activity, one can determine the mean value of the normal population and choose a range of one or more standard deviations from the mean to provide for greater certainty as to the absence of false positives and false negatives. Conveniently, from one to three standard deviations, preferably about two standard deviations is employed from the arithmetic mean, so that the normal range covers four standard deviations from the mean ($\pm 2SD$). The statistics may be further refined by providing for further subdivisions to determine normal values, such as dividing the patient groups by age, sex, or other statistically significant criteria. Values outside of the normal range, either high or low, particularly high, are indicative of a change in disease activity to an exacerbation, while values restoring the ratio to the normal range are indicative of a remission. Thus, by monitoring changes in the indicated ratios, one can predict with reasonable probability the onset of an exacerbation or a remission and relate this to the appropriate therapeutic regimen.

The antibodies which find use are antibodies, particularly monoclonal antibodies, specific for one or more epitopes of each of a plurality of surface membrane proteins. Monoclonal antibodies are employed which provide for distinguishing two subsets of T-cells, CD4+ and CD8+ cells. Conveniently, these monoclonal antibodies may be obtained by immunizing an appropriate host, conveniently a mouse, with a HPB-ALL T cell line (human peripheral blood—acute lymphocytic leukemia) and screening for antibodies specific for detecting CD4+ or CD8+ cell associated antigens, such as the Tp55 helper T cell-associated antigen and Tp32 suppressor T cell-associated antigen, respectively.

The antibodies to the other membrane surface proteins associated with differentiation may be obtained by immunization of an appropriate host with peripheral blood large granular lymphocytes or with T cells activated by mitogens, including alloantigens.

To prepare monoclonal antibodies, the host will normally be given booster shots, the host's spleen isolated and fusions carried out with the spleens in accordance with conventional techniques. (See, for example, Kennett et al., Monoclonal Antibodies, New York:Plenum Press, 1980, and references contained therein.)

The mouse antibodies may be any of the immunoglobulin types, for the most part they will be IgG, $\kappa$ of $\lambda$, usually $\kappa$, and may be IgG1, 2a, 2b, or 3.

Kits can be provided for detection of the cell populations to determine the previously indicated ratios. The kits may include the antibodies for one or both of the ratios and depending upon the particular protocol, may have the antibodies directed to the surface membrane proteins labeled or unlabeled. Where unlabeled, each of the antibodies to the surface membrane protein will usually be from a different host, so that labeled anti-immunoglobulin may be employed, which will bind to only one of the antibodies to allow for detection of the presence of the particular epitopic site. Alternatively, one of the antibodies may be conjugated with a ligand, e.g. biotin, in which case a fluorescer conjugated receptor, e.g. fluorescing avidin, is employed.

The monoclonal antibodies may be provided in a single composition, conveniently lyophilized and combined with appropriate additives, such as stabilizers, photobleach retardants, buffers, e.g. Tris, phosphate, etc. where the amount of antibody will be reconstituted prior to use to provide the desired concentration of antibody. Usually, the number of different fluorescers which will be present in a single mixture will be not greater than about six, more usually not greater than about four, generally ranging from two to four, preferably from two to three. Thus, where the ratio is dependent upon the analysis of the presence of two epitopic sites, one can provide one or two mixtures of antibodies depending upon the ability to distinguish between the fluorescence of the different antibodies. Fluorescent combinations of particular interest include fluorescein and phycoerythrin, phycoerythrin and allophycocyanin, fluorescein and Texas Red, etc. Other materials which may be included with the antibodies or in combination in the kit include lymphocyte separation medium, photobleach retardants, and various washing buffers, such as phosphate-buffered saline optionally containing bovine serum albumin.

The following examples are offered by way of illustration and not by limitation.

EXPERIMENTAL MATERIALS AND METHODS

Patients

All patients with MS satisfied the Schumacher criteria (Schumacher et al., Ann. N.Y. Acad. Sci. (1965) 122:552) for clinically definite disease. Stable MS was defined as three or more months of stable clinical state with an overall disability rating of less than three on the Kurtzke Disability Status Scale (Kurtzke, Neurology (Minneap) (1965) 15:654). Acute relapses were defined as definite neurological changes occurring over a period of one to five days in a patient previously documented as stable. Chronic progressive MS was defined as steady dissemination of disease in space and time with a monophasic course. Normal control subjects consisted of hospital and laboratory personnel. Neurological disease controls were chosen from patients with strokes, Alzheimer's disease, Parkinson's disease, or essential tremors, conditions which are believed to be nonimmunologic in nature. The MS groups consisted of 12 patients with acute exacerbations, 25 stable patients, and 8 patients with chronic progressive disease. There were 38 normal control subjects and 28 with other neurological diseases (Table I). Of the patients in acute relapse, three were tested serially.

Cell Preparations. Ten to 20 ml of peripheral blood was drawn into a heparinized tube or syringe, diluted 1:2 in RPMI 1620 tissue culture medium, and layered on lymphocyte separation medium (Litton Bionetics). After centrifugation, interface mononuclear cells were washed twice and resuspended at $1 \times 10^7$ cells/ml in RPMI medium containing 2% fetal bovine serum and 15 mM HEPES buffer.

Development of Monoclonal Antibodies 60.3. The 60.3 MAb ($IgG_{2a/k}$) to a common leukocyte cell surface antigen (Lp95-150/CDw18) has been described (Beatty et al., 1983, supra). It is expressed on most peripheral blood and bone marrow leukocytes and reacts with 95,000, 130,000, and 150,000 dalton polypeptides. The 60.3 antibody was prepared by immunizing an eight-week old female Balb/c mouse three times at two week intervals with T cells activated by alloantigen and maintained in T cell growth factor. Procedures for the fusion of immune spleen cells with the mouse myeloma line Balb/c MOPC2 NS1/1 are given in Appendix I. Hybridoma culture supernatants were screened for blocking of cytotoxic T-lymphocyte (CTL) effector function.

3AC5. Balb/c male mice were immunized three times with human peripheral blood large granular lymphocytes. (For fusion protocol, see Appendix I.) Using FACS IV analysis and indirect immunofluorescence, a MAb reactive with more than 60% of lymphocytes was selected. The antigen detected by 3AC5 is a 220,000 dalton polypeptide, Lp220. (See, Calchau and Fabre, 1984, In: Leukocyte Typing, ed., Bernard et al., p. 507, Springer-Verlag, Berlin, for a description of an antibody which reacts with the same antigen.) The antibody made in $IgG_{2a}/k$.

G17-2 and B10-1. Cell lines producing MAb to the (CD4) Tp55 helper T cell associated antigen (G17-2) and CD8 Tp32 suppressor T cell associated antigen (G10-1) were developed. Anti $T_h$ antibody G17-2.6 was derived from a cell fusion using $9 \times 10^7$ immune Balb/c mouse spleen cells and $1.8 \times 10^7$ cells of the NS-1 line. Spleen donors were immunized i.v. −3 weeks and −2 weeks with $1 \times 10^7$ cells of a HPB-ALL T cell line, and boosted i.v. three days prior to the fusion with $3 \times 10^7$ HPB-ALL. Positive clones were selected based on cell sorter histogram patterns seen with indirect immunofluorescence using supernatants and a FITC-goat F(ab')$_2$ anti-mouse IgG second step reagent. The $T_s$ antibody G10-1.1 was derived from a fusion of $1.7 \times 10^8$ immune Balb/c mouse spleen cells and $2 \times 10^7$ NS-1 myeloma cells. Spleen donors were immunized i.p. with $3 \times 10^6$ HPB-ALL cells −4 weeks, −3 weeks, −2 weeks and boosted i.v. three days before the fusion. Screening for positive culture was based on cell sorter histogram patterns as described above. (For fusion protocol, see Appendix I.)

Conjugation of MAb with Fluorescein (FITC) and Phycoerythrin (PE). MAb purified by DEAE-Sephacryl fractionation were conjugated with fluorescein using fluorescein-5-isothiocyanate (Goding, J. Immunol. Methods 13:215, 1976) or with (*Porphyra yesoensis*) R-phycoerythrin (PE) using SPDP (Oi et al., J. Cell. Biol. (1982) 93:981). Conjugated antibodies were used at two doubling dilutions above their titration end points on lymphocytes as measured by FACS IV analysis.

Two Color Flow Cytometry. Flow cytometry with a modified FACS IV cell sorter (Becton Dickinson) and quantitative two color analyses were performed. Cells ($5 \times 10^5$) in 50 $\mu$l were incubated for 30 min. on ice with fluorescein and/or PE-conjugated MAb, washed twice and then passed through 0.45 $\mu$m Nitex filter just prior to analysis. A 488 $\mu$m laser line was used, and a 560 $\mu$m dichroic mirror (Becton Dickinson) split the emission wave lengths. Additional 580 $\mu$m longpass and 540 $\mu$m shortpass filters (Ditric Optics, Hudson, MA) were placed in front of the red (PE) and green (fluorescein) photomultiplier tubes, respectively. A compensator was used to correct any residual spillover of green and red signals. Forward and right angle scatter gates were set on lymphocytes and to exclude other leukocytes.

Analysis of data. 40,000 cells/sample were analyzed and recorded on floppy discs. T cell subsets were quantitated. The CD4+ cells, as measured by their reaction with PE-G17-2, (OKT8 may also be used, Ortho Diagnostics Systems, Inc.) were split by the FITC-3AC5 MAb which divides the CD4+ subset into Lp220+ CD4+ cells and Lp220− CD4+ cells. $T_{s/c}$ cells were measured as CD8+ cells by their reaction with PE-G10-1 MAb. (OKT4 may also be used, Ortho Diagnostics Systems, Inc.) Using this antibody alone two populations of CD8+ cells are discerned, one subset has low levels of the CD8 antigen ($CD8^{dull}$), the other, high levels of CD8 antigen ($CD8^{bri}$). The CD8+ cells could be subdivided into three populations by FITC-60.3 MAb. FITC-60.3 divided the $T_{s/c}$ cells into Lp95-$150^{dull}$ $CD8^{bri}$, Lp95-$150^{bri}$ $CD8^{bri}$, and Lp95-$150^{bri}$ $CD8^{dull}$. Using the ND624 Dual Parameter Multichannel Data Analysis System (Nuclear Data, Inc., Schaumberg, IL 60196), percentages of total lymphocytes were obtained for each of the subsets. The following ratios were calculated: The $T_h/T_s$ (CD4+/CD8+) ratio; a $T_h$ subset ratio (percent Lp220− CD4+ cells/ Lp220+ CD4+ cells); and a $T_s$ subset ratio of the $CD8^{bri}$ $T_s$ cells only (% Lp95-$100^{bri}$ $CD8^{bri}$/% Lp95-$100^{dull}$ $CD8^{bri}$).

The mean and standard deviations (S.D.) of the ratios obtained for each sample group were calculated. Individuals with ratios 2 or more SD from the mean were designated "abnormal." Comparisons of "abnormal" and "normal" frequencies of each group were assessed by $X^2$ analysis.

TABLE I

Neurologic Diseases Other Than MS

| Diagnosis | Number |
|---|---|
| Parkinson's Disease | 8 |
| Amyotropic Lateral Sclerosis | 3 |
| Myasthenia Gravis | 2 |
| Alzheimer's Disease | 2 |
| CVA (cerebral vascular accident) | 2 |
| Alcoholic Neuropathy | 2 |
| TIA (transient ischemic attack) | 2 |
| Diabetic Neuropathy | 1 |
| Familial Tremor | 1 |
| Chronic Polymyositis | 1 |
| Spastic Paraplegia | 1 |
| Seizure | 1 |
| Meige's Syndrome | 1 |
| Frederich's ataxia | 1 |
| Total | 28 |

TABLE II

Subset Ratios in Normal Individuals and Patients With Neurologic Diseases

| | Ratio | | | | |
|---|---|---|---|---|---|
| | $\frac{CD4^+ Lp220-X}{CD4^+ Lp220^+}$ | | | $\frac{CD8^{bri} Lp95-150^{bri}}{CD8^{bri} Lp95-150^{dull}}$ | |
| Group Number | Abnl[1] h/l[2] | | Normal | Abnl[1] h/l[2] | Normal |
| Normal (38) | 2 (5) | 2 (5) | 36 (95) | 2 0 (5) (0) | 36 (95) |
| Inactive MS[4] nonacute (33) | 4 (12) | 1 (3) | 28 (85) | 11 6 (33) (18) | 16 (40) |
| Active Acute MS[5] (12) | 10 (83) | 0 (0) | 2 (17) | 9 1 (75) (8) | 2 (17) |
| Other Neurologic diseases (28) | 5 (18) | 2 (7) | 21 (75) | 14 0 (50) (0) | 14 (50) |

[1]CD4 ($T_h$) subset ratio: abnormal >2 standard deviation (<0.4 and >1.6); CD8 ($T_s$) subset ratio: abnormal >2 standard deviation (<0.3 and >1.5).
[2]h = high = >2SD l = low = <2SD
[3]Percent of total
[4]Includes: chronic stable, chronic progressive (no new symptoms), and remitting relapsing (in remission).
[5]Includes active chronic progressive and acute remitting relapsing. Three individuals have serial samples.

APPENDIX I

Cell Hybridization Method

1. Combine $9.0 \times 10^7$ fresh immune spleen cells and $1.5 \times 10^7$ NS-1 in serum containing RPMI media. Spin at 1000 rpm for five minutes in a 50 ml glass round-bottom screw-cap tube.
2. Aspirate all media and gently resuspend in 1-1.5 ml 50% PEG.
3. Spin at 1200 rpm for 10 minutes.
4. Immediately add 10-15 ml serum-free RPMI down sides of tube; gently swirl to bring pellet off bottom.
5. Spin at 1000 rpm for five minutes.
6. Add 20 ml RPMI, 15% FCS with HAT and then 20 ml of thymocyte ($2 \times 10^8$ total) in HAT. $5 \times 10^6$ thymocyte per ml final concentration.
7. 40 ml is divided into aliquots of 0.2 ml/well in two microliter plates.

Feed at day five by aspirating 0.1 ml of media and replacing with 0.1 ml of fresh RPMI, 15% FCS, with HAT. Feed every other day in this manner. Hybrids grow slowly at first and then more rapidly. Assay when master wells are approximately 40% confluent.

It is evident from the above results, that the conventionally measured $T_h/T_s$ (CD4+/CD8+) ratio is of little value in acute MS, while by measuring specific subsets of $T_h$ or $T_s$ cells, one can detect changes in status of a patient suspected of having multiple sclerosis or having multiple sclerosis, particularly as a prognosticator of an exacerbation or remission. The study involved a total of 111 individuals, of which 38 were healthy volunteers, 33 were MS patients with inactive disease, 12 were acute MS patients, and 28 were patients with other neurologic diseases. It was found that the percent of CD4+ Lp220+ cells dropped precipitously at a high frequency in acute MS patients leading to an elevated ratio of CD4+ Lp220−/CD4+ Lp220+ cells. The elevated $T_h$ ratios in acute MS were significantly different from those observed in normals ($p<0.001$), inactive MS (p 21 0.001), or other neurologic diseases ($p<0.001$). These results are highly significant even when conservative cutoff points are used. The $T_h$ subset ratio therefore appears to be a sensitive indicator of abnormal immune status, unlike the $T_h/T_s$ ratio which has been conventionally measured in immunologic disease.

In three acute relapsing MS patients, serial samples were obtained. Patient #1 had an abnormal $T_h$ subset ratio (2.0) five days pre-exacerbation. She was clinically normal at that time. One day post-exacerbation, her $T_h$ ratio rose to 3.9. Patient #2 had active disease ($T_h$ ratio equal 1.3) and ten days later was hospitalized with an acute exacerbation ($T_h$ ratio equal 4.7). Patient #3 has a severe chronic progressive disease ($T_h$ ratio equal 3.4) which clinically is getting worse (four weeks later, $T_h$ ratio equal 4.4). These data support the conclusion that an elevated $T_h$ ratio can correlate with deteriorating clinical status.

$T_s$ cells were divided into $CD8^{bri}$ and $CD8^{dull}$ cells. The $CD8^{bri}$ cells were further divided into the subset $Lp95-150^{bri}$ and $Lp95-150^{dull}$ and the ratio of $Lp95-150^{bri}$ to $Lp95-150^{dull}$ calculated. Acute MS groups had the highest proportion of abnormal individuals. The proportion of acute MS with high $T_s$ subset ratios was significantly different from age match normals ($p<0.001$), barely different from the inactive MS ($p<0.05$), and not different from other neurologic disease groups ($p<1$). The inactive/chronic MS ($p<0.01$) and other neurologic disease groups ($p<0.001$) were also different from normals indicating that this ratio is not as specific to MS as the $T_h$ subset ratio, but may nonetheless provide a better abnormal immune status marker than the $T_h/T_s$ subset ratio.

In a second testing of normal individuals (n=22), a significant difference between the $T_s$ subset ratio of younger individuals (age 20-45) and older individuals (46-70) was observed. This suggests that a high number of "abnormal" $T_s$ subset ratio values (50%) in the "other" neurological disease group is age related, rather than disease related, since the median age in that group was 69 years. The median age for both MS groups was 38 years and similar to the first control group.

It is evident from the above results, that meaningful information can be obtained providing for predictability of changes in disease activity in multiple sclerosis patients or individuals suspected of having multiple sclerosis. Thus, monitoring can be employed with therapeutic regimens to minimize side effects while maintaining protection from dysfunction and continued cellular deterioration from the disease.

Although the foregoing invention has been described in some detail by way of illustration and example for purposes of clarity of understanding, it will be obvious that certain changes and modifications may be practiced within the scope of the appended claims.

What is claimed is:

1. A method for the diagnosis and monitoring of disease activity in cases of immunologic disease, which comprises determining a ratio comprising the level of at least one of the T-cell subsets, CD4+ or CD8+, divided by the relative presence or absence of surface membrane proteins, other than CD4 or CD8, associated with cellular differentiation, and relating the ratio to a predetermined range as indicative of a normal or abnormal condition.

2. A method according to claim 1, wherein the immunologic disease is multiple sclerosis.

3. A method according to claim 1 or 2, wherein said ratio comprises the level of CD4+ cells divided by high or low levels of Lp220+ cells.

4. A method according to claim 1 or 2, wherein said ratio comprises the level of CD8+ cells divided by high or low levels of Lp95-150+ cells.

5. A method according to claim 1 or 2, wherein fluorescent labels are used for said determination employing a fluorescence activated cell sorter.

6. A method according to claim 5, wherein at least one fluorescer is a phycobiliprotein.

7. A kit comprising containers of at least one of a combination of differently fluorescent labeled monoclonal antibodies, a first combination being a monoclonal antibody for detecting CD4+ cells and a monoclonal antibody for detecting a membrane surface protein, other than CD4 and CD8, related to cellular differentiation; and a second combination being a monoclonal antibody for detecting CD8+ cells and a monoclonal antibody for detecting a surface membrane protein, other than CD4 and CD8, associated with differentiation, wherein said fluorescent label may be covalently bound to said monoclonal antibodies or non-covalently bound through complex formation.

8. A kit according to claim 7, wherein said first combination includes a monoclonal antibody to Lp220 and said second combination includes a monoclonal antibody to Lp95-150.

9. A kit according to claim 8, wherein at least one fluorescer is a phycobiliprotein and another fluorescer is fluorescein.

10. A method for the diagnosis and monitoring of disease activity in persons having or suspected of having an immunologic disease, said method comprising determining the cellular ratio of CD4+ Lp220−/CD4+ Lp220+ or of CD8+ Lp95-150+/CD8+ Lp95-150−; and relating the ratio to a predetermined range as indicative of a normal or abnormal condition.

11. A method according to claim 10, wherein fluorescent labels and a fluorescence activated cell sorter are used for said determination.

12. A method according to claim 11, wherein two fluorescent labels are used for said determination.

13. A kit for the diagnosis and monitoring of disease activity in persons having or suspected of having an immunological disease, which comprises containers of at least one of a combination of differently fluorescent labeled monoclonal antibodies, a first combination being a monoclonal antibody for detecting CD4+ cells and a monoclonal antibody reactive with Lp220; and a second combination being a monoclonal antibody for detecting CD8+ cells and a monoclonal antibody reactive with Lp95-150.

14. A method for the diagnosis and monitoring of disease activity in persons having or suspected of having multiple sclerosis, which comprises:
determining the presence of at least one of the T-cell subsets, CD4+ or CD8+;
further determining the relative presence or absence of Lp220 or Lp95-150, whereby a ratio is determined comprising the presence of surface membrane proteins associated with cellular differentiation relative to the presence of at least one of said T-cell subsets; and
relating the ratio to a predetermined range as indicative of a normal or abnormal condition.

* * * * *